United States Patent

Amey

(12) United States Patent
(10) Patent No.: US 6,245,946 B1
(45) Date of Patent: Jun. 12, 2001

(54) PROCESS FOR CONVERSION OF CYCLODODECANE-1,2-DIONE TO CYCLODODECANONE

(75) Inventor: Ronald Lee Amey, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/633,941

(22) Filed: Aug. 8, 2000

(51) Int. Cl.$^7$ .................................... C07C 45/00
(52) U.S. Cl. .......................... 568/343; 568/338; 568/347
(58) Field of Search .................................. 568/338, 343, 568/347

(56) References Cited

U.S. PATENT DOCUMENTS

| | | | |
|---|---|---|---|
| 3,374,270 | 3/1968 | Hausen et al. | 260/586 |
| 3,652,674 | 3/1972 | Hausen et al. | 260/586 |
| 5,892,123 | 4/1999 | Anderson et al. | 568/361 |

FOREIGN PATENT DOCUMENTS

| | | |
|---|---|---|
| 199 15894 C1 | 4/1999 | (DE) . |
| 74030827 | 8/1974 | (JP) . |
| 03115247 | 5/1991 | (JP) . |

OTHER PUBLICATIONS

L. L. Klinova, A. I. Papukova, N.M. Madygina, L.N. Bychkova, and D.T. Egorova, Catalytic Hydrogenation of Epoxycyclododecane, Production of Organic Products, Papers of Giap, Moscow, 79–84, 1982.

F.A. Chernyshkova, D.V. Mushenko, Production of Cyclododecanone by Isomerization of Epoxycyclododecane on Pd and Rh, *Neftekhimiya*, XVI, No. 2, 250–254, 1976.

*Primary Examiner*—Johann Richter
*Assistant Examiner*—J. Parsa

(57) ABSTRACT

Catalytic process for converting cyclododecane-1,2-dione to cyclododecanone.

2 Claims, No Drawings

PROCESS FOR CONVERSION OF CYCLODODECANE-1,2-DIONE TO CYCLODODECANONE

FIELD OF THE INVENTION

This invention relates to a process for converting cyclododecane-1,2-dione to cyclododecanone using selected catalysts.

BACKGROUND OF THE INVENTION

It is known that butadiene can be converted to dodecanedioic acid (DDDA) by process which involves converting the butadiene to cyclododecatriene (CDDT), reducing the CDDT to cyclododecane (CDD), oxidizing the CDD to a mixture comprising cyclodecanol (A, for alcohol) and cyclodecanone (K, for ketone) in the presence of a boric acid catalyst, and finally oxidizing the mixture of K and A to DDDA using nitric acid. In this process, the K and A mixture contains about 80–90% A and 10–20% K.

Recently, for environmental reasons, it has been proposed to perform the above reaction without boric acid, to eliminate boron-containing waste. A boron-free process for the manufacture of a mixture of cyclododecanone (K) and cyclododecanol (A) is disclosed in U.S. Pat. No. 5,892,123. When the above-described reaction is performed without boric acid, the K and A mixture contains about 10–25% A and 75–90% K. The mixture also contains undesirable epoxides and cyclododecanedione impurities. Cyclodecanedione is particularly objectionable, because it imparts a fluorescent canary yellow color to the final K and A mixture, which is further used in the manufacture of lauryl lactam and, ultimately, of Nylon 12. It can also deactivate catalysts used to convert the K and A mixture into lauryl lactam. Its presence in the K and A mixture can also impart undesirable odors to fragrance chemicals made using the mixture or pure cyclododecanone. Accordingly, there is a need for a process which can be used to convert cyclododecanedione to substances such as cyclododecanone, which do not have these undesirable effects.

Although two references (Klinova, L. L.; Patsukova, A. I.; Malygina, N. M.; Bychkova, L. N.; Egorova, L. T., *Pr-vo Organ. Produktov. M.* (1982) 79–84 and Chernyshkova, F. A.; Mushenko, D. V., *Neftekhimiya* (1976), 16(2), 250–4) disclose the reaction of cyclododecane epoxide with active nickel (i.e., nickel reduced in the presence of hydrogen) or with palladium or rhodium (metal-catalyzed isomerization to cyclododecanone), these references do not disclose the use of such catalysts to convert a cyclodecane-1,2-dione to cyclododecanone.

The use of copper or nickel catalysts for conversion of C12 alcohol or C12 alcohol/ketone mixtures to C12 ketone is known in the art. For example, U.S. Pat. No. 3,374,270 discloses catalytic dehydrogenation of C12 alcohol to C12 ketone using copper supported on an aluminum oxide carrier, U.S. Pat. No. 3,652,674 discloses the same reaction using a barium-promoted copper chromite catalyst, JP 74030827 discloses dehydrogenating C12 alcohol to C12 ketone using a nickel on kieselguhr catalyst, and JP 03115247 discloses vapor-phase dehydrogenation of the alcohol to the ketone using a copper/zinc catalyst. None of these references, however, discloses the use of catalysts to convert a C12 diketone to a C12 ketone.

BRIEF SUMMARY OF THE INVENTION

The present invention is a process for converting cyclododcane-1,2-dione to cyclododecanone comprising contacting the cyclododcane-1,2-dione with a copper-containing or nickel-containing catalyst. The catalyst may be supported or unsupported.

In a preferred embodiment the present invention is a process for increasing the amount of cyclododecanone in a mixture comprising cyclododecanone and cyclododecane-1,2-dione, comprising contacting the mixture with a copper-containing or nickel-containing catalyst.

DETAILED DESCRIPTION OF THE INVENTION

Suitable starting materials for the process of the present invention include the following: cyclododecane-1,2-dione or mixtures which contain this diketone as an undesirable impurity, for example, the C12 oxidate (C12 ketone/alcohol mixture) obtained by the boron-free process of U.S. Pat. No. 5,892,123. The invention is also suitable for the catalytic decomposition of cyclododecane epoxides or cyclododecane epoxides that are found in such mixtures. The product of the catalysis of cyclododecane-1,2-dione is cyclododecanone.

Suitable catalysts for the process of the present invention include the following: copper-containing or nickel-containing catalysts, including activated copper or nickel catalysts such as the commercially available Raney® (trademark of W. R. Grace) metal catalysts, copper chromite catalysts, copper/zinc catalysts, supported copper catalysts, or supported nickel catalysts. Many of these catalysts are supplied commercially as the metal oxide and need to be activated by reduction either prior to use or during the start-up of the reaction (in situ reduction). This reduction can be carried out by known methods using externally added hydrogen or by the presence of C12 alcohol in the feed mixture. The catalysts can also contain other added metals as stabilizers, promoters, or activators (for example barium added to copper chromite; zinc added to Raney copper). The catalysts can be powders or small granules for slurry operation; larger granules, tablets, extrudates, spheres, or other shapes for fixed bed operation.

The process conditions for carrying out the present invention are not particularly critical. Preferred conditions are as follows.

The reaction may be run at atmospheric pressure, slightly above or slightly below atmospheric pressure. Pressure selection depends on the starting material, the mode of operation and the available equipment.

The temperature may be from about 160 C. to about 270 C. Temperatures of 200 to 250 C. are preferred; 220–250 C. is most preferred.

The reaction may be run in batch mode using a slurry catalyst in a stirred reactor or in a continuous mode using a fixed-bed catalyst and reactor. The fixed-bed mode can operate downflow in trickle bed operation (liquid feed and product), upflow in flooded bed operation (liquid feed and product), or in vapor phase operation (upflow or downflow is acceptable). The reaction can also be run as a reactive distillation. Fixed bed operation is generally preferred because of the ease of operation on a commercial scale.

The catalyst loading in slurry mode can be from about 0.1 to about 4 wt. % of catalyst relative to the organic starting material. 0.1 to 1.0 wt. % is preferred; 0.25 to 0.75 wt. % is most preferred.

The feed flow rate for fixed bed mode is not critical. The liquid hourly space velocity (LHSV) can be about 0.4–1.5 $h^{-1}$, with about 0.8–1.0 $h^{-1}$ being preferred. The actual selection depends on the specific starting material, the specific catalyst chosen and the reactor design.

The process can be performed by co-feeding gas with the organic feed. Nitrogen, argon, or other inert gases are added for safety purposes and/or to prevent air from entering the system and deactivating the catalyst. Hydrogen can be added because it helps prolong the catalyst life and improves the decomposition of the epoxide and the diketone, even at very low levels.

EXAMPLES

Example 1

Reaction of non-boron process C12 ketone/alcohol with copper chromite powder, slurry mode The feed material was 74.2% cyclododecanone, 22.9% cyclododecanol, 1.2% cyclododecane epoxide, 1500 ppm (parts per million) cyclododecane-1,2-dione, and is a brilliant, fluorescent canary yellow.

25 g of the above feed was mixed with 1 g of commercially available Engelhard Corp.) Cu-1106 P copper chromite catalyst powder. The mixture was heated for two hours at 250 C., cooled to room temperature and analyzed by GC. The product, water-white, is 95.4% cyclododecanone, 2.7% cyclododecanol (unreacted), 0% cyclododecane epoxide, 0.4% cyclododecene, and 63 ppm cyclododecane-1,2-dione.

Example 2

Reaction of non-boron process C12 ketone/alcohol with copper chromite extrudate, reactive distillation mode The feed material was the same as that used in Example 1.

6.8 g of Engelhard Cu-1 230 E, copper chromite extrudate (1/16 inch) was placed in a small glass distillation column to form a catalyst bed 4 inches deep and 3/8 inch in diameter. The feed mixtures was heated to 250 C. and a slight vacuum was pulled on the column using a small vacuum pump such that the feed material vaporized and passed through the catalyst bed before being collected. The product, water-white, was 91% C12 ketone, 7% unreacted C12 alcohol, 0.2% C12 epoxide, 100 ppm C12 diketone.

Example 3

Reaction of non-boron process C12 ketone/alcohol with copper chromite extrudate, fixed bed mode The feed material was the same as that used in Example 1.

A ¾ inch inside diameter glass tube was filled with 48.4 g (8 inch depth) of Engelhard Cu-1230 E copper chromite 1/8" extrudate. The catalyst bed was operated downflow, liquid feed as a trickle bed. The catalyst was activated following the procedure of Engelhard Corp. prior to use. Briefly, the procedure involved treating the catalyst with increasing heat and hydrogen over a period of time. The bed was heated by an external electrical heater to 250 C. The organic feed was supplied to the bed at 2 cc/min in the presence of 4 cc/min. nitrogen gas (an inert added for safety purposes and to maintain catalyst activity). Product samples were taken every hour and analyzed. The results are shown in the table below.

| Sample Hour | % Ketone | % Alcohol |
| --- | --- | --- |
| 1 | 90.3 | 5.1 |
| 2 | 94.6 | 3.2 |
| 3 | 88.5 | 7.7* |
| 4 | 88.5 | 10.3* |
| 5 | 91.6 | 6.2 |
| 6 | 90.7 | 7.5 |
| 7 | 92.4 | 5.5 |
| 8 | 93.8 | 3.9 |
| 9 | 93.5 | 4.1 |
| 10 | 93.1 | 4.7 |
| 11 | 92.9 | 5.1 |
| 12 | 93.3 | 4.6 |
| 13 | 93.3 | 4.6 |
| 14 | 93.3 | 4.2 |
| 15 | 93.8 | 3.8 |
| 16 | 93.8 | 4.0 |
| 17 | 92.6 | 4.9 |

*Sample shows lower conversion due to a plug in the reactor and a temperature drop across the bed.

All samples were water-white and analyzed for 0% cyclododecane epoxide and non-detectable cyclododecane-1,2-dione (<50 ppm).

Example 4

Reaction of non-boron process C12 ketone/alcohol with granular Raney Ni, fixed bed mode The feed material was 74.7% cyclododecanone, 16% cyclododecanol, 0.3% cyclododecane epoxide, 509 ppm cyclododecane-1,2-dione, and the balance was cyclododecane. (See Example 3 for comparison.)

The reactor was loaded with 66.4 g (5¾ inch bed depth) of Raney nickel 5886 (W. R. Grace) and the catalyst bed was heated to 165 C. Organic feed was fed to the reactor at 1 cc/min in the presence of nitrogen gas at 4 cc/min. The reaction was run for 8 hours and samples were collected at 1 hour intervals and then analyzed.

Average product composition over the 8 hr sample period was 78% cyclododecanone, 11% cyclododecanol, 0.06% epoxide, and non-detectable levels of cyclododecane-1,2-dione.

Example 5

Reaction of cyclododecane-1,2dione with copper chromite catalyst in an inert solvent A solution of 10 wt. % cyclododecane-1,2dione (85% purity) in cyclododecane was mixed with 1 wt. % (relative to the C12 diketone) of Engelhard Cu-1106 P copper chromite catalyst powder. The mixture was stirred under nitrogen at 250 C. for 4 hrs. Samples were analyzed at various intervals. Product results were normalized and the cyclododecane solvent peak was subtracted from the final data. Results are shown in the table below.

| Time | Dione % | Ketone % | Alcohol % | Cyclododecene, % |
|---|---|---|---|---|
| 0 | 85 | ND* | ND* | ND* |
| 30 min | 42 | 28.6 | 1.5 | 14.0 |
| 60 min | 35.4 | 32.3 | 2.1 | 14.4 |
| 90 min | 29.2 | 36.3 | 4.3 | 14.9 |
| 120 min | 21.8 | 40.4 | 5.2 | 15.0 |
| 180 min | 20.6 | 49.7 | 5.2 | 17.8 |
| 240 min | 20.4 | 50.2 | 2.0 | 16.2 |

*ND = non-detectable

What is claimed is:

1. A process for converting a cyclododecane-1,2-dione to cyclododecanone comprising contacting the cyclododecane-1,2-dione with a copper-containing or nickel-containing catalyst.

2. A process for increasing the amount of cyclododecane in a mixture comprising cyclododecanone-1,2-dione and cyclododecanone, comprising contacting the mixture with a copper-containing or nickel-containing catalyst.

* * * * *

UNITED STATES PATENT AND TRADEMARK OFFICE
CERTIFICATE OF CORRECTION

PATENT NO. : 6,245,946 B1
DATED : June 12, 2001
INVENTOR(S) : Ronald Lee Amey

It is certified that error appears in the above-identified patent and that said Letters Patent is hereby corrected as shown below:

<u>Claim 2,</u>
Line 7, change "cyclododecane" to -- cyclododecanone --.
Line 8, change "cyclododecanone-1,2-dione" to -- cyclododecane-1,2-dione --.

Signed and Sealed this

Twenty-sixth Day of March, 2002

Attest:

JAMES E. ROGAN
*Attesting Officer*  *Director of the United States Patent and Trademark Office*